United States Patent [19]

Kwak

[11] 4,175,564
[45] Nov. 27, 1979

[54] NASAL GASTRIC TUBE INSERTION GUIDE AND METHOD

[76] Inventor: In S. Kwak, 2846 Galahad Dr., Atlanta, Ga. 30345

[21] Appl. No.: 885,609

[22] Filed: Mar. 13, 1978

[51] Int. Cl.² .............................................. A61M 27/00
[52] U.S. Cl. ................................. 128/350 R; 128/351
[58] Field of Search ............... 128/350, 348, 349, 351, 128/214.4, DIG. 26, 1

[56] References Cited

U.S. PATENT DOCUMENTS

| | | | |
|---|---|---|---|
| 3,559,643 | 2/1971 | Pannier, Jr. et al. ............ | 128/214.4 |
| 3,754,554 | 8/1973 | Felbarg ................. | 128/351 |
| 3,853,130 | 12/1974 | Sheridan ......................... | 128/349 R |
| 4,068,658 | 1/1978 | Berman ............................ | 128/351 X |

*Primary Examiner*—Stephen C. Pellegrino
*Attorney, Agent, or Firm*—Robert B. Kennedy

[57] ABSTRACT

A guide for guiding a nasal gastric tube of preselected outside diameter into the esophagus and stomach of a patient for evacuation of stomach fluids. The guide comprises a tube formed with an end to end slit having an inside diameter greater than the nasal gastric tube outside diameter whereby the nasal gastric tube may be inserted into the guide tube through a guide tube end and subsequently extracted through the guide tube slit. In use, a nasal gastric tube is located in position within the nasopharynx with one tube end projecting out of the patient's nose and the other tube end projecting out of the patient's mouth. A longitudinally slit tubular guide is telescoped over the end of the nasal gastric tube projecting out of the patient's mouth. The free end of the tubular guide opposite the tubular guide end from which the nasal gastric tube emerges from the guide is inserted into the patient's esophagus. The tubular guide is then peeled from the nasal gastric tube by passing the nasal gastric tube through the tubular guide slit.

4 Claims, 7 Drawing Figures

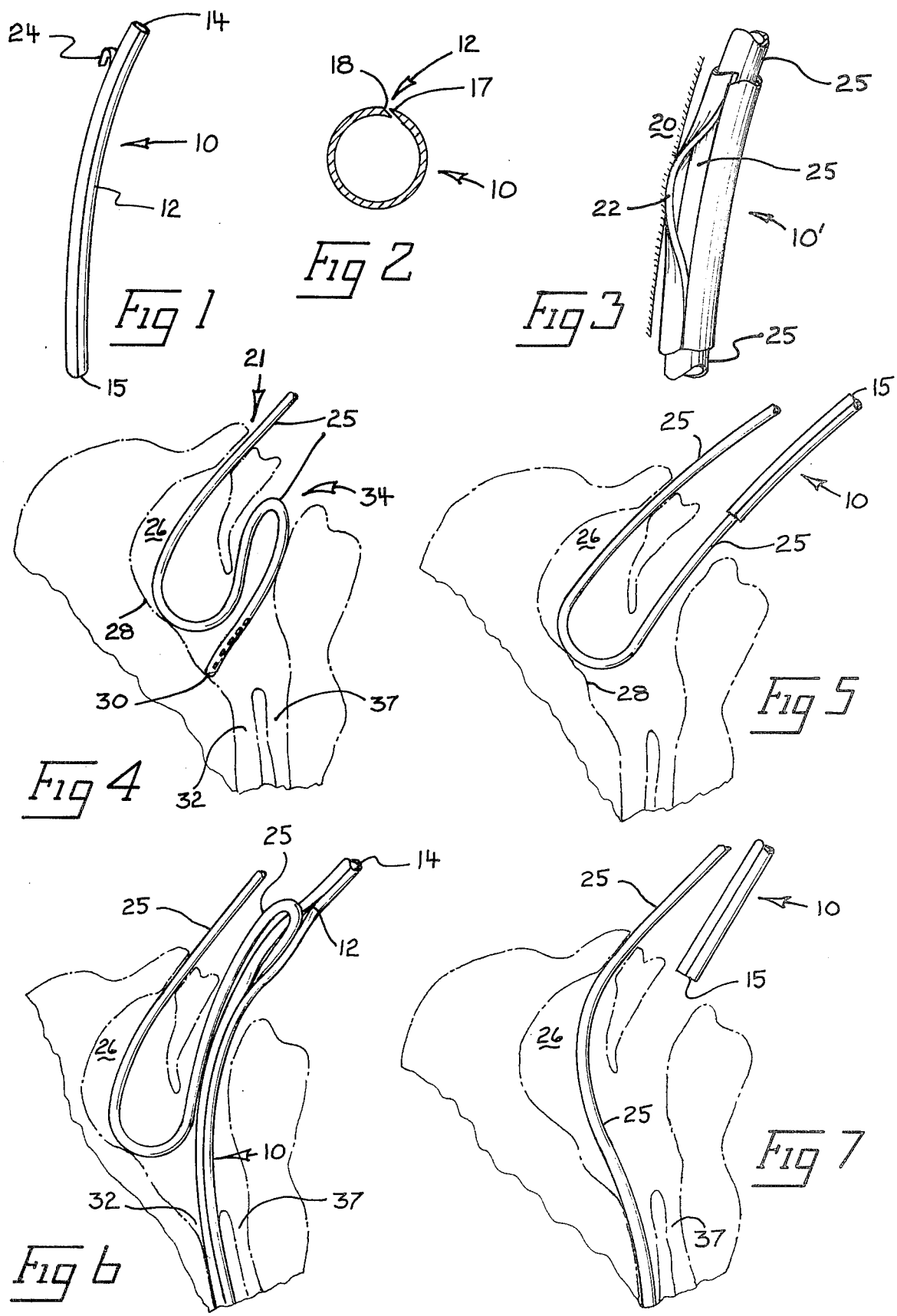

NASAL GASTRIC TUBE INSERTION GUIDE AND METHOD

BACKGROUND OF THE INVENTION

This invention relates to methods and means for inserting nasal gastric tubes into the stomachs of patients for evacuation of stomach fluids.

Post-surgical patient recovery often necessitates the continuous withdrawal of fluids from the patient's stomach. This is accomplished by the means of placing the perforated end of a tube within the stomach and applying a suction force to draw fluids out of the stomach and patient through the tube. Since the tube must ordinarily be left in place for a substantial period of time it is highly preferable to have the tube routed through the nasopharynx and nasal passages rather than exit through the mouth of the patient. Extension of the tube out through the mouth would be very discomforting to the patient over an extended period of time due to the gagging and coughing such a position initiates. A tube of size and flexibility to be routed through the nasopharynx, esophagus and into the stomach of a patient is termed a nasal gastric tube.

In positioning a nasal gastric tube within a patient the perforated tube end is first extended into the nose through the nasal passages and nasopharynx to a position adjacent to the larynx. Here the tube must be carefully routed into the esophagus rather than into the trachea in order to approach the stomach. This is a difficult and tedious task with many patients as when their nasopharynx is not smooth but stretched and wrinkled with age, and when the patient is under anesthesia. It thus often occurs that the tube, which is quite flexible in order to follow the body cavities smoothly, enters the trachea instead. When this occurs the tube must be partially withdrawn and attempts remade in guiding the tube into the esophagus. In other cases the tube end becomes lodged in abutment against the pharynx and begin to double up and fold into the mouth. Again attempts must be made to retrieve and re-route the nasal gastric tube into the esophagus.

The just described problems of repeatedly guiding a nasal gastric tube into the esophagus and stomach tends to cause nose bleeding and to traumatize the pharynx. In addition, substantial periods of time are often required in properly locating the nasal gastric tube. As previously stated, the nasal gastric tube must be soft and flexible but these very attributes impede placement.

To overcome these problems there has heretofore been developed several instruments designed to be inserted through the mouth into gripping engagement with the nasal gastric tube located adjacent the pharynx in order to guide it into the esophagus. U.S. Pat. Nos. 3,316,913 and 3,339,552 exemplify such instruments which generally take the form of metal clamps or forceps adapted to grip an end portion of the nasal gastric tube in guiding it into place. The use of forceps however is rather ineffectual since the entrance to the esophagus is located substantially below that area of the pharynx which may be easily visualized through the mouth. The metal forceps may also themselves traumatize the pharynx. In use they must be intermitantly and repeatedly released and moved up to higher portions of the tube and then re-gripped in urging the nasal gastric tube down step by step towards and into the esophagus. With each such relocation of the forceps time passes and the threat of pharynx traumatization increases.

Accordingly, it is a general object of the present invention to provide an improved method for guiding a nasal gastric tube into the esophagus and stomach of a patient for evacuation of stomach fluids.

Another object of the invention is to provide a method of guiding a nasal gastric tube into the esophagus and stomach of a patient without the use of forceps, clamps or the like.

Another general object of the invention is to provide an improved guide for guiding a nasal gastric tube into the esophagus and stomach of a patient.

Yet another object of the invention is to provide a guide of the type described which tends less to traumatize a patient's pharynx in operation than do the guides of the prior art.

SUMMARY OF THE INVENTION

In one preferred form of the invention a guide is provided for guiding a nasal gastric tube of preselected outside diameter into the esophagus and stomach of the patient for evacuation of stomach fluids. The guide comprises a tube formed with an end to end slit and with an inside diameter greater than the nasal gastric tube outside diameter whereby the nasal gastric tube may be inserted into the guide tube through a guide tube end and subsequently extracted through the guide tube slit.

In another preferred form of the invention a method is provided for guiding a nasal gastric tube into the esophagus and stomach of a patient for evacuation of stomach fluids. The method comprises the steps of locating the nasal gastric tube in position within the nasopharynx with one tube end projecting out of the patient's nose and the other tube end projecting out of the patient's mouth. A longitudinally split tubular guide is telescoped over the end of the nasal gastric tube projecting out of the patient's mouth. The free end of the tubular guide opposite the tubular guide end from which the nasal gastric tube emerges from the guide is inserted into the patient's esophagus. The tubular guide is then peeled from the nasal gastric tube by passing the nasal gastric tube through the tubular guide slit.

In yet another form of the invention a method is provided for guiding a nasal gastric tube into the esophagus and stomach of a patient for evacuation of stomach fluids. Here an arc-shaped tubular guide of preselected flexibility is passed into the nose, through the nasopharynx and into the esophagus of a patient. A nasal gastric tube of greater flexibility than the preselected flexibility is located in the tubular guide with a portion of the nasal tube located within the patient's esophagus. The tubular guide is then withdrawn from about the nasal gastric tube and from the patient.

BRIEF DESCRIPTION OF THE DRAWING

FIG. 1 is a perspective view of a nasal gastric tube embodying principles of the invention in one preferred form.

FIG. 2 is a cross-sectional view of the nasal gastric tube guide shown in FIG. 1.

FIG. 3 is a perspective view of a portion of a nasal gastric tube guide with a radial slit together with a nasal gastric tube housed therewithin.

FIGS. 4–7 illustrate an operative sequence in practicing a method of the invention using the nasal gastric tube guide shown in FIGS. 1 and 2.

DESCRIPTION OF THE PREFERRED EMBODIMENTS

Referring now in more detail to the drawing there is shown in FIGS. 1 and 2 a nasal gastric tube guide 10 which comprises an arc-shaped tube of some 32 to 36 cm length and of some 8.5 mm inside diameter and 9 mm outside diameter for use with adult patients. The tube is composed of a flexible material such as rubber or plastic. It may, for example, be formed of the same material as that of a standard tracheal tube. The tube is formed with a slit 12 which extends from one tube end 14 to the other tube end 15. As shown in FIG. 2 the slit is formed along a plane which passes to one side of the axis of the tube itself. In other words it is not radial.

One purpose of this slit orientation is to inhibit traumatization of the pharynx in use. With the slit oriented non-radially one portion 17 of the tube to one side of the slit overlays another portion 18 of the tube which defines the other side of the slit. It will be seen that portion 17 is thus quite thin and thus highly pliable while the other portion 18 is seen to present a smooth, rounded exterior surface where it merges with the remaining radial portion of the tube body. So configured neither side edge of the tube defining the slit 12 tends to harm or irritate the skin tissue against which is brought. For example, if these edges of the guide are brought into contact with skin tissue then portion 17, being highly flexible, will tend to flex away from rather than cut the tissue. Portion 18 with its smooth, rounded exterior surface will also tend not to harm the tissue. This avoids the problem which would be otherwise encountered as shown in FIG. 3 were the slit to be located on a plane radial to the axis of the tubular guide. In such a case a slit defining edge portion 22 of guide 10 could injure the pharynx tissue 20 were it bent as from kinking from its normally cylindrical configuration. Finally, the guide is provided with a pull tab 24 located radially opposite this slit adjacent guide end 14.

With reference next to FIGS. 4–7 a method of guiding a nasal gastric tube into the esophagus and stomach of a patient in accordance with the present invention is shown which in this case utilizes the just described nasal gastric tube guide. In FIG. 4 a standard nasal gastric tube 25 is seen to have been inserted through the nose 21 of a patient and through the nasopharynx 26 into end contact with the patient's pharynx 28. As a result of this contact with the pharynx the perforated end 30 of the nasal gastric tube has become lodged in place without proper entry into the esophagus 32. Further insertion of the tube into the nose is thus seen to have caused the tube to bend double out through the patient's mouth 34.

In accordance with a present method the folded bend or perforated end of the nasal gastric tube is manually gripped pulling end 30 completely out of the mouth to the position shown in FIG. 5. With end 30 now protruding from the patient's mouth the nasal gastric tubular guide 10 is telescoped easily over the end portion 30 of the nasal gastric tube. Next, the free end 15 of the guide is inserted back into the mouth of the patient and routed into the esophagus as shown in FIG. 6. Since the flexibility of the guide tube is substantially less than that of the nasal gastric tube itself, and since the tubular guide is arc-shaped as is the guide insertion path, this procedure of inserting the guide into the esophagus is easily accomplished.

With the guide tube now in the position shown in FIG. 6 the end 30 of the nasal gastric tube itself is also now located within the bounds of the upper portion of the esophagus. Next, the guide 10 is removed from the patient's mouth and the nasal gastric tube by pulling hand tab 24 away from slit 12. This causes the nasal gastric tube to laterally exit the guide tube slit in the axial region adjacent the pull tab. This is continued down along the slit as shown in FIG. 6 by simultaneously slowly withdrawing the guide from the esophagus out of the patient's mouth while the nasal gastric tube is squeezed out of the guide tube slit 12. Finally, as shown in FIG. 7 the guide 10 is completely removed from the patient and the nasal gastric tube itself extended into the stomach and straightened in the area over the pharynx into a long term operative configuration and location.

In an alternate mode of operation an arc-shaped tubular guide may be inserted through the nose itself down over the pharynx and into the esophagus with the nasal gastric tube located within or subsequently inserted through the guide and into the stomach. The guide itself is then removed out of the nose. This method is less desirable than the previously described mode due to the relatively small clearance of passage of the guide through the nasal passages. However it is possible where the nasal passages of the particular patient are sufficiently large. In this case the guide may be merely slipped from an end of the nasal gastric tube during guide removal.

It should be understood that flexible tubes or catheters have heretofore been snuggly housed within a longitudinally split sheath as exemplified by U.S. Pat. Nos. 3,853,130 and 3,774,605. Such has been done however purely for ease of catheter removal from a sterile environment prior to catheter implant. Thus, both the structure and function of these sterile sheaths have differed substantially from that of the nasal gastric tube guide of the present invention. Structural resemblence of the present guide to the metallic forceps and clamps heretofore used is nill. The method is also seen to be entirely different from and superior over those of the prior art as previously described. It should be further understood that the just described embodiments merely illustrate principles of the invention in selected preferred forms. Many modifications, additions and deletions may, of course, be made thereto without departure from the spirit and scope of the invention as set forth in the following claims.

I claim:

1. A guide for guiding a nasal gastric tube of preselected outside diameter into the esophagus and stomach of a patient for evacuation of stomach fluids and with said guide comprising an arcuately shaped tube formed with an end to end slit and having an inside diameter greater than the nasal gastric tube outside diameter, and a pull tab mounted to the exterior of said guide tube radially opposite said slit, whereby the nasal gastric tube may be inserted into the guide tube through a guide tube end and subsequently extracted through the guide tube slit by pulling the nasal gastric tube and the guide pull tab apart as the arcuately shaped guide tube is introduced into the patient's mouth and esophagus.

2. A method of guiding a nasal gastric tube into the esophagus and stomach of a patient for evacuation of stomach fluids comprising the steps of:
 (a) locating the nasal gastric tube in position within the nasopharynx with one tube end projecting out of the patient's nose and the other tube end projecting out of the patient's mouth;

(b) telescoping a longitudinally slit tubular guide over the end of the nasal gastric tube projecting out of the patient's mouth;

(c) inserting the free end of the tubular guide opposite the tubular guide end from which the nasal gastric tube emerges from the guide into the patient's esophagus; and (d) peeling the tubular guide from the nasal gastric tube by passing the nasal gastric tube through the tubular guide slit.

3. A nasal gastric tube guide method in accordance with claim 2 wherein step (a) the nasal gastric tube is located within the nasopharynx by insertion into the nose, through the nasal passages, nasopharynx and pharynx and out of the patient's mouth.

4. A nasal gastric tube guide method in accordance with claim 2 wherein step (d) the tubular guide is peeled while being extracted from the patient's esophagus and mouth.

* * * * *